United States Patent
Showalter et al.

(10) Patent No.: US 6,403,931 B1
(45) Date of Patent: Jun. 11, 2002

(54) SLIDE HEATER CALIBRATOR AND TEMPERATURE CONVERTER APPARATUS AND METHOD

(75) Inventors: Wayne Showalter; William L. Richards; Charles D. Lemme, all of Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 09/415,026

(22) Filed: Oct. 7, 1999

(51) Int. Cl.⁷ .................................................. H05B 1/02
(52) U.S. Cl. ....................... 219/486; 219/483; 219/497; 374/1; 435/809
(58) Field of Search ................................. 219/497, 506, 219/483, 486, 501, 499; 374/1, 121, 133; 422/64, 67; 435/3, 283.1, 286.1, 809, 303.1

(56) References Cited

U.S. PATENT DOCUMENTS

| | | | |
|---|---|---|---|
| RE35,716 E | * 1/1998 | Stapleton et al. | 435/3 |
| 5,998,767 A | * 12/1999 | Kersch et al. | 219/390 |
| 6,115,441 A | * 9/2000 | Douglass et al. | 377/25 |
| 6,169,442 B1 | * 1/2001 | Meehan et al. | 327/513 |
| 6,179,466 B1 | * 1/2001 | Peuse et al. | 374/128 |
| 6,183,693 B1 | * 2/2001 | Bogen et al. | 422/64 |
| 6,191,399 B1 | * 2/2001 | Van Bilsen | 219/497 |

FOREIGN PATENT DOCUMENTS

| | | |
|---|---|---|
| EP | 0 812 621 A | 12/1997 |
| EP | 0 884 394 A | 12/1998 |
| WO | 99 44030 | 9/1999 |

\* cited by examiner

*Primary Examiner*—Mark Paschall
(74) *Attorney, Agent, or Firm*—McDonnell Boehnen Hulbert & Berghoff (57) ABSTRACT

Apparatus and methods for controlling heaters in an automated biological apparatus are provided. The heating system has a conversion buffer in between the desired temperature generator and the heating controller. The heating controller is in communication with a slide temperature sensor, which provides feedback to the heating controller, and a heater. Because the slide temperature sensor may inaccurately reflect the actual temperature on the slide, the heating controller may inaccurately heat the slide to an undesired temperature. Thus, the conversion buffer compensates for potential inaccuracies of the heating controller. The desired temperature generator sends the "desired temperature" for the slide to the conversion buffer. The conversion buffer converts the "desired temperature" to an "adjusted temperature" and sends it to the heating controller. The heating controller then controls the heater based upon the "adjusted temperature" and the heating sensor. The conversion buffer may be generated during calibration of the machine. Similarly, the temperature, which is sensed from the slide temperature sensor, may be adjusted to reflect the actual temperature for the slide.

11 Claims, 10 Drawing Sheets

SLIDE HEATER CALIBRATOR AND TEMPERATURE CONVERTER APPARATUS AND METHOD

FIELD OF THE INVENTION

The present invention is directed to apparatus for use in diagnostic molecular pathology and, more particularly, to such an apparatus used for the automated staining and/or treating of tissue samples mounted on microscope slides.

BACKGROUND OF THE INVENTION

Molecular pathology is the examination at a molecular level of the DNA, mRNA, and proteins that cause or are otherwise associated with disease. From this examination important information about patient diagnosis, prognosis, and treatment options can be elucidated. The practice of molecular pathology is generally divided into two main areas: (i) analysis of DNA, mRNA, and proteins in intact cells (in-situ), and (ii) analysis of these biological materials after they have been extracted from tissues. The first category, to which the present invention is directed, has the advantage that it allows the pathologist or scientist to study the histopathologic architecture or morphology of the tissue specimen under the microscope at the same time that the nucleic acid or proteins are being assayed. These techniques include immunohistochemistry (IHC) which looks at proteins, in-situ hybridization (ISH) which looks at nucleic acids, histochemistry (HC) which looks at carbohydrates, and enzyme histochemistry (EHC) which looks at enzyme chemistry. For example, ISH can be used to look for the presence of a genetic abnormality or condition such as amplification of cancer causing genes specifically in cells that, when viewed under a microscope, morphologically appear to be malignant. ISH is also useful in the diagnosis of infectious diseases as it allows detection not only of a microbial sequence but also of precisely which cells are infected. This may have important clinicopathologic implications and is an effective means to rule out the possibility that positive hybridization signal may have come from an adjacent tissue of no clinical concern or from blood or outside contamination.

IHC utilizes antibodies which bind specifically with unique epitopes present only in certain types of diseased cellular tissue. IHC requires a series of treatment steps conducted on a tissue section or cells (e.g. blood or bone marrow) mounted on a glass slide to highlight by selective staining certain morphological indicators of disease states. Typical steps include pretreatment of the tissue section to remove the paraffin and reduce non-specific binding, retrieval of antigens masked by cross-linking of the proteins from the chemical fixatives, antibody treatment and incubation, enzyme labeled secondary antibody treatment and incubation, substrate reaction with the enzyme to produce a fluorophore or chromophore highlighting areas of the tissue section having epitopes binding with the antibody, counterstaining, and the like. Most of these steps are separated by multiple rinse steps to remove unreacted residual reagent from the prior step. Incubations can be conducted at elevated temperatures, usually around 37° C., and the tissue must be continuously protected from dehydration. ISH analysis, which relies upon the specific binding affinity of probes with unique or repetitive nucleotide sequences from the cells of tissue samples or bodily fluids, requires a similar series of process steps with many different reagents and is further complicated by varying temperature requirements.

In view of the large number of repetitive treatment steps needed for both IHC and ISH, automated systems have been introduced to reduce human labor and the costs and error rate associated therewith, and to introduce uniformity. Examples of automated systems that have been successfully employed include the NEXES® and Gen II® staining systems available from Ventana Medical Systems (Tucson, Ariz.) as well as the system disclosed in U.S. Pat. No. 5,654,199 to Copeland et al. These systems employ a microprocessor controlled system including a revolving carousel supporting radially positioned slides. A stepper motor rotates the carousel placing each slide under one of a series of reagent dispensers positioned above the slides. Bar codes on the slides and reagent dispensers permits the computer controlled positioning of the dispensers and slides so that different reagent treatments can be performed for each of the various tissue samples by appropriate programming of the computer.

The aforementioned staining systems include either a hot air blower or a heat lamp to warm the samples above laboratory ambient temperatures for steps requiring elevated temperatures. Heating the slide improves staining quality by acceleration of the chemical reaction and can permit a reaction temperature more closely matching body temperature (about 37° C.) at which antibodies are designed to react. While such convection or radiant heating systems have been generally suitable for IHC, which is antibody based, they are less suitable for ISH, which is nucleic acid based and requires higher and more precise temperature control. In order to denature the DNA double helix of both the target sample and the probe so as to render them single stranded, the temperature must be raised above the melting point of the duplex, usually about 94° C. At the same time it is imperative that the sample not be overheated past 100° C. as doing so destroys cell morphology making it difficult to view under a microscope. Precise temperature control is also required in ISH to effect probe hybridization at the desired stringency. The selected temperature must be low enough to enable hybridization between probe and template, but high enough to prevent mismatched hybrids from forming. It would be desirable, therefore, to have an automatic tissue staining apparatus which can control the temperature of reactions with enough precision for most ISH applications.

In addition, even if heaters are used in combination with the slide holders, the heating of the slides may be inaccurate. For example, U.S. Pat. No. 5,645,114 to Bogen et al. discloses a dispensing assembly adapted to carry a plurality of microscope slides. Individual slide holders containing resistive heating units are provided. However, with the assembly taught by Bogen et al., the actual temperature of the slide placed on top of the heater may be different than the temperature set for the heater. This is due to the fact that different heaters have different heating profiles (i.e., there may be variations in temperature on the platform of the heater). This is also due to the fact that the temperature sensor, which determines whether the heater is heating to the correct temperature, is not placed in the same position as that of the slide. Instead, the temperature sensor is typically placed in an area away from the slide, such as on the underside of the heater, thereby potentially resulting in an inaccurate heating of the slides. It would be desirable, therefore, to have an automatic tissue staining apparatus wherein a slide can be accurately heating to a specific predetermined temperature.

SUMMARY OF THE INVENTION

The present invention is directed to apparatus and methods for automatically staining or treating multiple tissue samples mounted on microscope slides so that each sample can receive an individualized staining or treatment protocol even when such protocols require heating. More specifically, the apparatus is a computer controlled, bar code driven, staining instrument that automatically applies chemical and biological reagents to tissue or cells mounted or affixed to standard glass microscope slides. Up to 20 slides are mounted in a circular array to a carousel which rotates, as directed by the computer, placing each slide under one of a series of reagent dispensers positioned above the slides. Each slide receives the selected reagents (e.g. DNA probe) and is washed, mixed and/or heated in an optimum sequence and for the required period of time. Tissue sections so stained or treated are then removed from the apparatus by the user to be viewed under a microscope by a medical practitioner who reads the slide for purposes of patient diagnosis, prognosis, or treatment selection. The computer controlled automation permits use of the apparatus in a "walk-away" manner, i.e. with little manual labor.

Slide temperature control is accomplished by a heating system according to the present invention. The heating system, in one embodiment, has a conversion buffer in between the desired temperature generator and the heating controller. The heating controller is in communication with a slide temperature sensor, which provides feedback to the heating controller, and a heater. Because the slide temperature sensor may inaccurately reflect the actual temperature on the slide, the heating controller may inaccurately control the heater and heat the slide to an undesired temperature. Thus, the conversion buffer compensates for potential inaccuracies of the heating controller. The desired temperature generator sends the "desired temperature" for the slide to the conversion buffer. The conversion buffer converts the "desired temperature" to an "adjusted temperature" and sends it to the heating controller. The heating controller then controls the heater based upon the "adjusted temperature" and the heating sensor. The conversion buffer may be generated during calibration of the machine. Similarly, the temperature which is sensed from the slide temperature sensor may be adjusted to reflect the actual temperature for the slide.

A key advantage of the present invention is that the slides can be accurately heated to a specific predetermined temperature.

Another advantage of the present invention is that it allows the calibration of the slide heaters so that during operation of the heaters, the slide is heated to the proper temperature.

With the foregoing and other objects, advantages and features of the invention that will become hereinafter apparent, the nature of the invention may be more clearly understood by reference to the following detailed description of the invention, the appended claims and to the several views illustrated in the drawings.

DETAILED DESCRIPTION OF THE INVENTION

Figure 1:
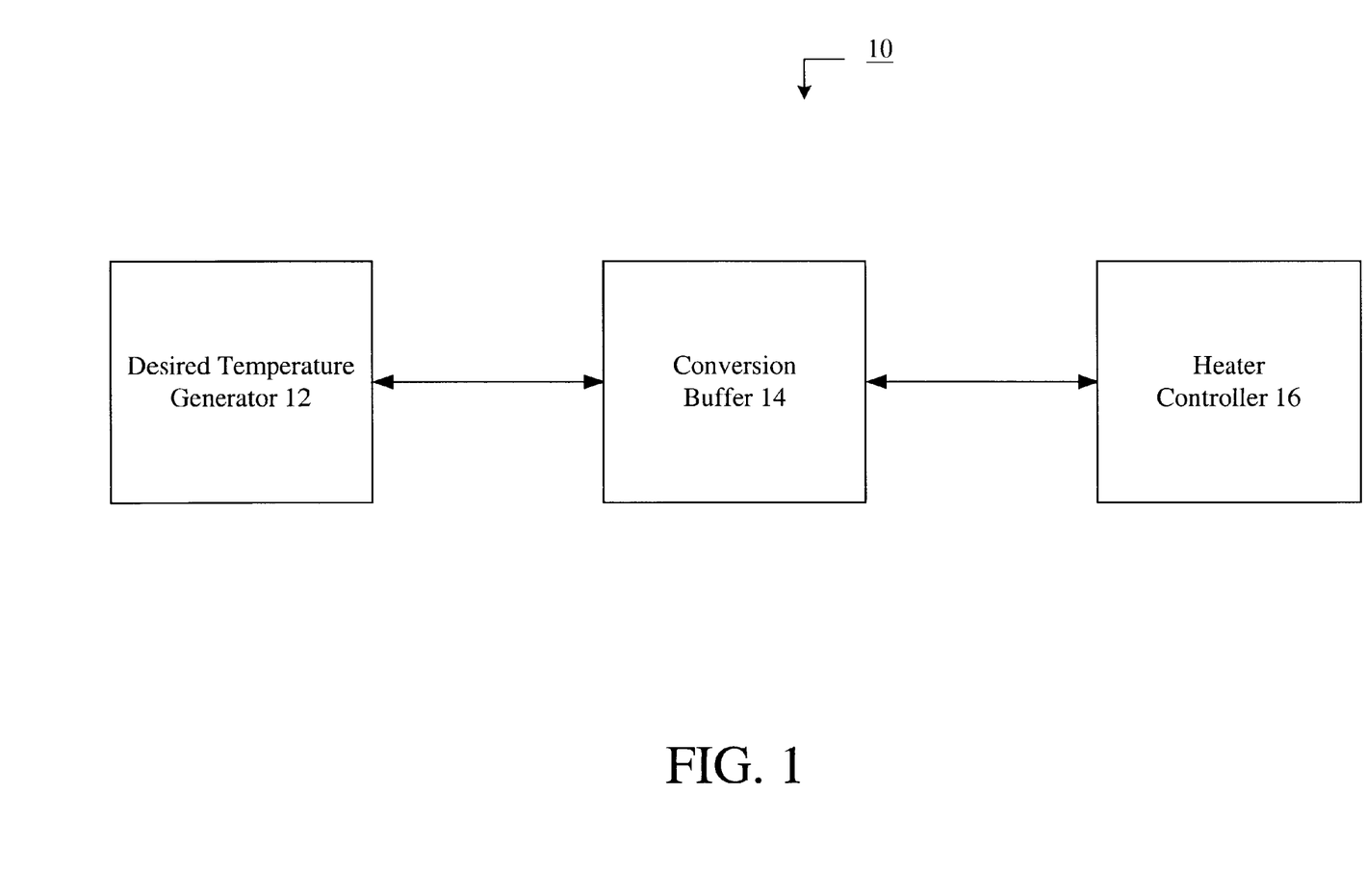
FIG. 1 is a block diagram of the heating system.

Referring now in detail to the drawings wherein like parts are designated by like reference numerals throughout, there is illustrated in FIG. 1 a block diagram of the heating control system 10. Heating control system 10 is designed to operate within a machine that automatically stains or otherwise treats tissue mounted on microscope slides with nucleic acid probes, antibodies, and/or reagents associated therewith in the desired sequence, time and temperature. One example of an automated apparatus is disclosed in U.S. application Ser. No. 08/995,052 filed on Dec. 19, 1997, which is hereby incorporated by reference in its entirety. Examples of an individually controlled heating system are disclosed in U.S. application Ser. No. 60/076,198 filed on Feb. 27, 1998, U.S. application Ser. No. 09/259,240 filed on Feb. 26, 1999, to PCT application Ser. No. PCT/US99/04181 filed on Feb. 16, 1999, each of which are hereby incorporated by reference in their entirety. The heating control system 10 is, in one embodiment, a subsystem of the automated apparatus. Tissue sections so stained or treated by the automated apparatus are then to be viewed under a microscope by a medical practitioner who reads the slide for purposes of patient diagnosis, prognosis, or treatment selection.

As shown in FIG. 1, the heating control system 10 is composed of a desired temperature generator 12, a conversion buffer 14 and a heater controller 16. The desired temperature generator is used to input the desired temperature (or setpoint temperature of the heaters). The input of the desired temperature may be done via an operator or via an automated means, such as reading a barcode on a slide and determining based upon the barcode, the heating requirements of the slide.

As disclosed in U.S. application Ser. No. 09/259,240 and PCT application Ser. No. PCT/US99/04181, the heaters may be individually controlled so that a multitude of desired temperatures may be input for each of the heaters. However, the application of the invention is not limited to individually controlled slide heaters. Because heaters may vary, each heater should be calibrated, whether or not it is individually controlled.

The desired temperature generator 12 is in communication with the conversion buffer 14 which converts the desired temperature into an adjusted temperature. As discussed in the background of the invention, the actual temperature of the slide may be different from the sensed temperature. The conversion buffer compensates for this difference. The conversion buffer, in one embodiment, is generated through a calibration routine, as described subsequently. The conversion buffer 14 is in communication with the heater controller 16, which receives the adjusted temperature. The heater controller 14 controls the heaters by using a slide temperature sensor, as described subsequently. Likewise, temperatures which are sensed by the temperature sensor are converted through the conversion buffer, so that the actual temperature on the slide is properly reported.

Figure 2:
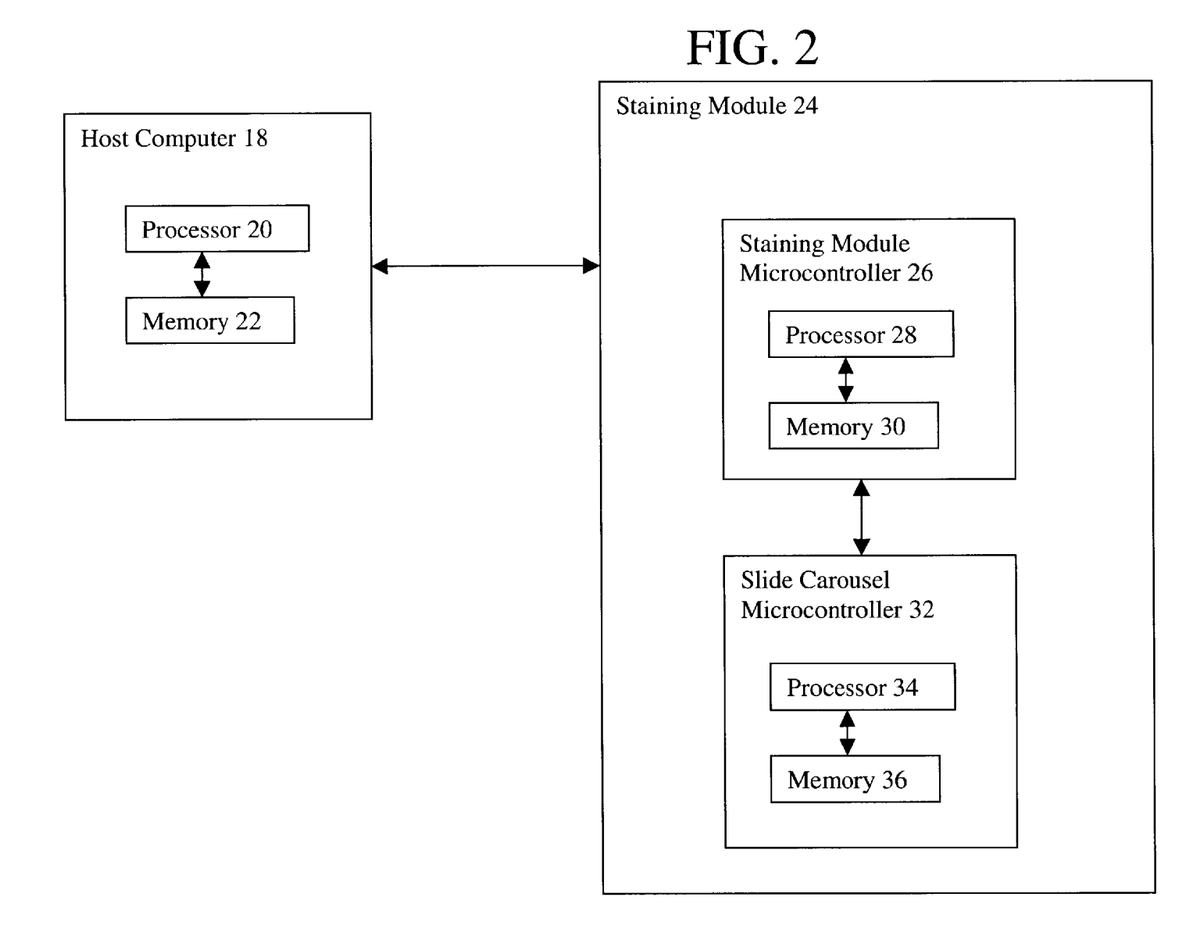
FIG. 2 is a block diagram of a host computer and staining module.

In a preferred embodiment, the heating control system 10 functions as a subsystem of a larger module. Referring to FIG. 2, there is shown a block diagram of host computer 18 and a staining module 24. The host computer 18 includes a processor 20, which in a preferred embodiment is a microprocessor, and a memory 22. The staining module includes a staining module microcontroller 26 and a slide carousel microcontroller 32. The staining module microcontroller 26 also includes a processor 28 and a memory 30. The slide carousel microcontroller 32 likewise includes a processor 34 and a memory 36.

The staining module reads barcodes on the slides contained in the slide carousel (not shown). These barcodes are sent to the host computer, which generates protocols, including the heating protocols, based upon the barcodes on the slides. The host computer 18 then downloads the protocols to the staining module 24. Thus, the host computer 18 of FIG. 2 operates as the desired temperature generator 12 of FIG. 1 in that the host computer 18 determines the desired temperature of each of the slides on the slide carousel.

Except during the calibration, which described subsequently, the host computer 18 is concerned only with on-slide temperatures (actual temperatures on the slide). It requests on-slide temperatures from the staining module microcontroller 26. The host computer 18 sends new on-slide temperature setpoints (or desired temperatures) to the staining module microcontroller 24 as required. The host computer 18 does not need to know what the conversion buffer 14 does.

The staining module microcontroller 26 receives the protocols sent from the host computer 18. The processor 28 reads memory 30 of the staining module microcontroller to determine the conversion necessary. Thus, the staining module microcontroller 26, including the processor 28 and memory 30, acts as the conversion buffer 14 of FIG. 1 in that it converts the desired temperature, as determined by the host computer 18, into an adjusted temperature.

The slide carousel microcontroller 34, which controls the operation of the slides including rotation of the carousel and controlling of the slide heaters, receives instructions from the staining module microcontroller 26 in its control of the carousel and slide heaters. The slide carousel microcontroller 32, in one embodiment, operates as the heater controller 16 of FIG. 1.

The slide carousel microcontroller 32 is concerned only with actual sensor temperatures (the output of the slide temperature sensor). The slide carousel microcontroller 32 receives a temperature setpoint command from the staining module microcontroller 26 and applies heat to the heating element in order to maintain that temperature on the temperature sensor. Similar to the host computer 18, the slide carousel microcontroller 32 does not need to know what the conversion buffer 14 does.

The staining module microcontroller 26 is in between the host computer 18 and the slide carousel microcontroller 32. It retains two sets of calibration constants, one that is the inverse of the other. As described subsequently, in a preferred embodiment, each set of calibration constants is in the form of a line, that is, $y=mx+b$, where m is the slope of the line and b is the intercept of the line. When the host computer 18 sends a temperature setpoint request, the setpoint calibration constants are applied to compute the adjusted temperature setpoint. This adjusted temperature setpoint is sent to the slide carousel microcontroller 32 to use as the controlling setpoint. When a sensor temperature is received from the slide carousel microcontroller 32, the other set of calibration constants, the sensor calibration constants, are applied to it to compute the adjusted on-slide temperature. This adjusted on-slide temperature is sent to the host computer 18 when requested. Because of variations of the heaters, each individual slide has its own sets of calibration constants.

As shown in FIG. 2, there are three processors 20, 28, 34 and three memory devices 22, 30, 36 in the operation of the automated apparatus. This is due to the fact of separating the automated apparatus into different modules. However, a single processor and memory device can be used to function as the desired temperature generator 12, the conversion buffer 14 and the heater controller 16. Thus, depending on the needs of the system, a single or a plurality of processors and memory devices may be used.

Figure 3:
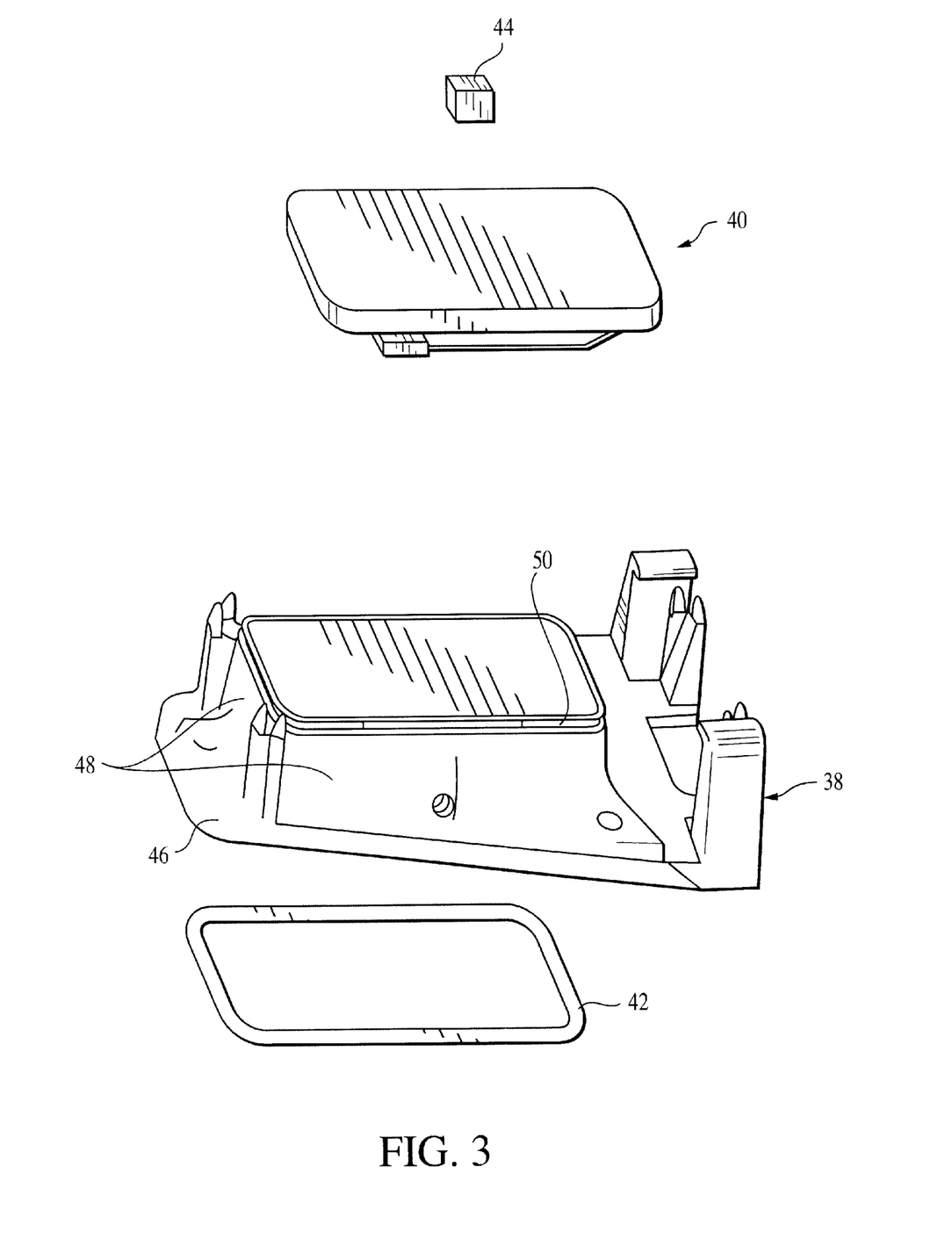
FIG. 3 is an exploded perspective view of the slide holder, o-ring, heater assembly and slide calibration sensor.

Referring to FIG. 3, there is shown an exploded perspective view of the slide holder 38, o-ring 42, heater assembly 40 and slide calibration sensor 44. The slide holder 38 serves as a platform for the heater assembly. The slide holder has a base 46 and sidewalls 48 with an upper ridge 50. The upper ridge 50 serves to contact the heater assembly 40. The heater assembly 40 include electronics which, after the heater assembly 40 is connected to the slide holder 38, are housed within the slide holder 38. The slide holder 38 is connected to the carousel (not shown) with an o-ring 42 abutting the bottom portion of the base 46. In this manner, the electronics contained in the heater assembly 40 are sealed within the slide holder 38. The automated biological apparatus, in a preferred embodiment, processes a multitude of slides simultaneously. Therefore, each slide has an o-ring, slide holder and heater assembly (including a plurality of heaters and a plurality of slide temperature sensors). In addition, during calibration, each slide has a slide calibration sensor.

Figure 4A:
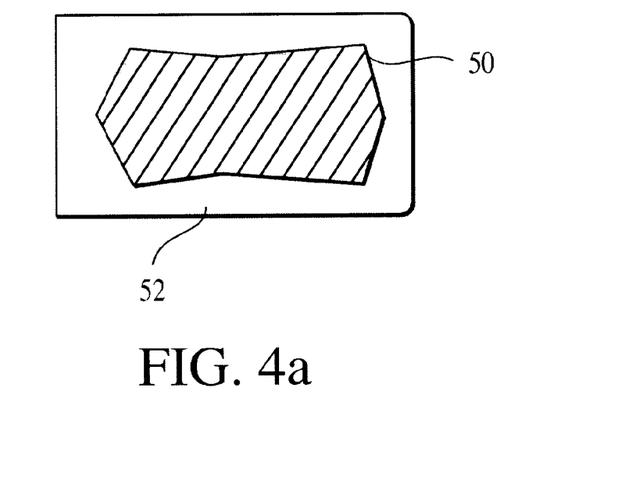
FIG. 4a is a bottom view of the heater profile of the heater assembly.
Figure 4B:
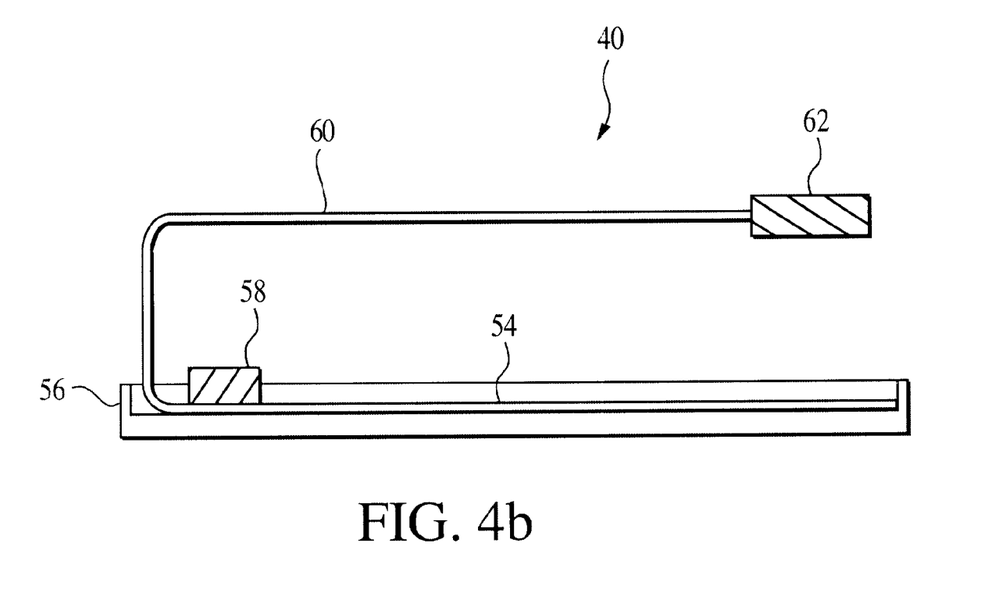
FIG. 4b is a cross section of the heater assembly.

Referring to FIG. 4a, there is shown a bottom view of the heater profile of the heater assembly 40. The profile shows an inner zone 50 and an outer zone 52. The inner and outer zones 50, 52 are configured so that the heating generated on the top of the heater assembly is generally uniform. Referring to FIG. 4b, there is shown a cross section of the heater assembly 40. The heater assembly 40 includes a heater 54 (in a preferred embodiment a KAPTON® heater centered side to side), a brass cup 56, a slide temperature sensor 58, a flex lead 60 and a connector 62. The slide temperature sensor 58, which is placed on the underside of the heater assembly 40, senses temperature. This placement of the slide temperature sensor on the underside is so that, after the heater assembly 40 is connected to the slide holder 38, the slide temperature sensor 58 is sealed and cannot be damaged. The temperature sensed by the slide temperature sensor 58 is communicated, via the flex lead 60 and the connector 62, to the processor 34 of the slide carousel microcontroller 32. The processor 34 determines, based on the output of the slide temperature sensor 58, the amount of heat necessary for the heater to generate, and accordingly sends instructions to the heater, via the flex lead 60. In this manner, temperature is controlled in the heater assembly 40. In addition, in the configuration of a plurality of slide heaters and slide temperature sensors, the heater controller is in communication with each of the slide heaters and each of the slide temperature sensors.

Figure 5A:
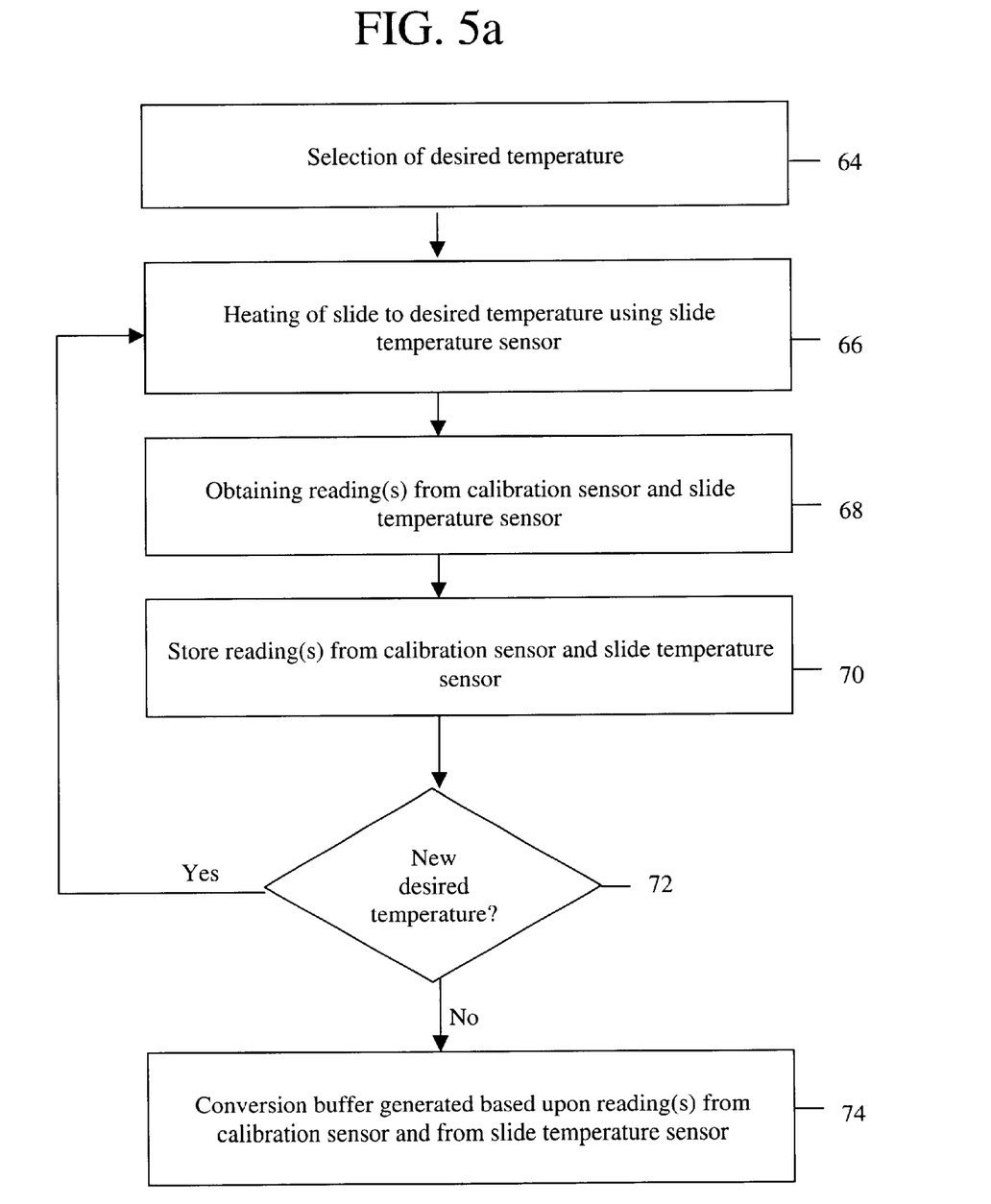
FIG. 5a is a flow chart of the calibration of the heating system for generating the conversion buffer.

As discussed previously, the slide sits on the upper side of the heater assembly 40. However, the temperature sensed is based upon a reading which is not where the slide is (i.e., the slide temperature sensor 58 is on the underside of the heater assembly 40). Thus, the slide temperature sensor 58 reading may be inaccurate, causing the slide to be heated to the wrong temperature. In order to compensate for this potential error, a conversion buffer 14 is generated during calibration of the machine. Referring to FIG. 5a, there is shown a flow chart of the calibration of the heating system for generating the conversion buffer. As shown at block 64, a desired temperature for the heater assembly is selected. The heater assembly is then heated to the desired temperature using the slide temperature sensor, as shown at block 66. As discussed previously, the heater controller 16 uses the slide temperature sensor to determine whether the heater assembly is at the proper temperature. For example, the desired temperature is sent to memory 36 of the slide carousel microcontroller 32. Processor 34 obtains the readings from the slide temperature sensor and, based upon the readings, turns the heater on or off.

At least one reading is then obtained from at the slide calibration sensor and at least one reading is obtained from the slide temperature sensor, as shown at block 68. In a preferred embodiment, a slide calibration sensor is placed in the position or section where the sample on the slide will sit on the upper side of the heater. The slide temperature sensor is placed in a different position or section from the slide calibration sensor. The slide calibration sensor, in the preferred embodiment, is a sensor that transmits its temperature via infrared. The infrared sensor does not sit on the sample of the slide, but rather senses, via infrared, what the temperature on the slide is during calibration. One example of an infrared temperature sensor is Everest Interscience, Inc. of Tucson, Ariz., Model 4000.4 gl. In an alternative embodiment, the slide calibration sensor is a sensor which directly contacts the sample on the slide (e.g., a thermistor sensor).

For additional accuracy, a plurality of readings may be taken from the calibration sensor and slide temperature sensor. The readings from the calibration sensor are the temperature that the sample would be exposed to. The readings for the calibration sensor and the slide temperature sensor are stored, as shown at block 70. If a new desired temperature is requested, then the process is repeated again, as shown at block 72. In the preferred embodiment, at least two desired temperatures are selected, with corresponding readings from the calibration sensor obtained.

Thereafter, the conversion buffer is generated based upon the readings from the calibration sensor and based upon the readings from the slide temperature sensor, as shown at block 74. In a preferred embodiment, a straight line (y=mx+b) is fit to the readings with the two variables (the slope m and the intercept b being calculated). The difference between the temperature of the sensor and the actual temperature on the top of the heater is a function of the actual temperature. Because of this, a line calibration curve is used to approximate the difference. Other statistical analyses may be generated based upon the readings from the calibration sensor, including a curve being fit to the readings. Alternatively, the conversion buffer may consist of a look-up table, which may be generated based upon the readings.

In an alternative embodiment, instead of storing the readings from the slide temperature sensor, the desired temperature is stored. Therefore, in calculating the conversion buffer, the readings from the calibration sensor are correlated to the desired temperature sent to the heater assembly.

Figure 5B:
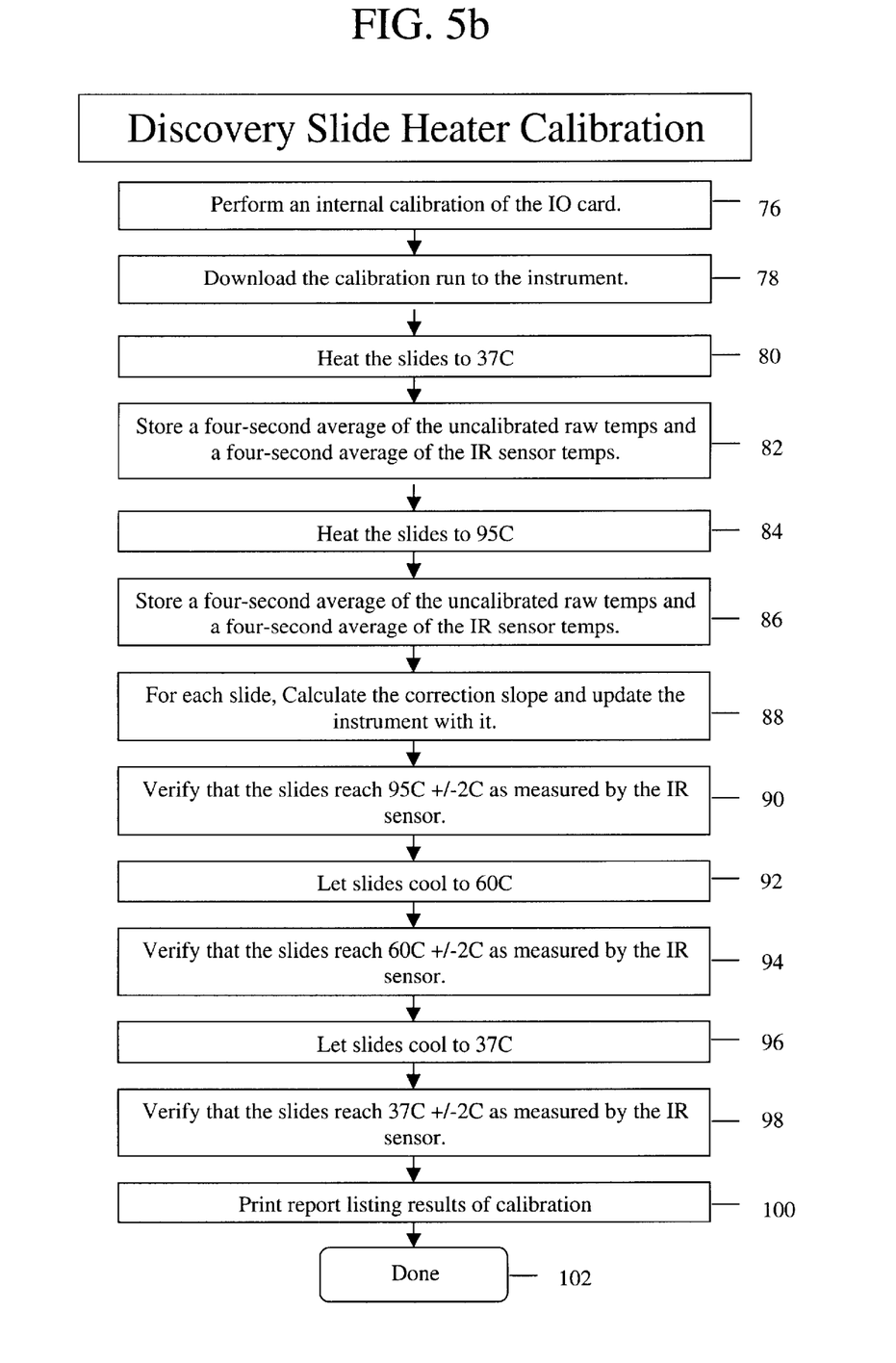
FIG. 5b is an expanded flow chart of one example of the calibration of the heating system for generating the conversion buffer.

Referring to FIG. 5b, there is shown an expanded flow chart of one example of the calibration of the heating system for generating the conversion buffer. An internal calibration is performed on the input/output (IO) card, as shown at block 76. Thereafter, the host computer 18 downloads the calibration run to the memory 30 of the staining module microcontroller 26, as shown at block 78. The processor 28 executes the program and directs the processor 34 of the slide carousel microcontroller 32 to heat the slides to 37° C., which is the first desired temperature, as shown at block 80. Each of the slides has a slide temperature sensor and calibration sensor. For each of the slides, a four-second average of the slide temperature sensor is stored (the uncalibrated raw temps) and a four-second average of the calibration sensor is stored (IR sensor temps), as shown at block 82. The slides are then heated to 95° C., which is the second desired temperature, as shown at block 84. A four-second average of the slide temperature sensor is stored (the uncalibrated raw temps) and a four-second average of the calibration sensor is stored (IR sensor temps), as shown at block 86. The conversion buffer for each slide is calculated using the correction slope and intercept (m and b). This information is sent to the staining module microcontroller 26, as shown at block 88, so that it may be stored in memory 30 for using during normal operation of the automated apparatus.

The conversion buffer is then verified by testing whether the slides reach the requested temperatures within certain tolerances. As shown at block 90, it is verified that the slides reached 95° C.+/−2° C. as measured by the calibration sensor. In particular, the desired temperature as sent from the calibration run is set at 95° C. The conversion buffer receives this desired temperature and determines an adjusted temperature. This adjusted temperature is sent to the heater controller 16. If the adjusted temperature, as calculated by the conversion buffer, does not produce a temperature on the slide within a certain tolerance, as determined by the slide calibration sensor, the conversion buffer was calibrated improperly, and an error message is sent. In the preferred embodiment, the tolerance is +/−2° C. so that if slide calibration sensor does not indicate an output of 95° C.+/−2° C., an error message is sent. The slides are then cooled to 60° C., as shown at block 92. In particular, the new desired temperature is programmed into the heater controller 16 as 60° C. Similarly, it is then verified that each of the slides reached 60° C.+/−2° C. as measured by the calibration sensor, as shown at block 94. The slides are then cooled to 37° C., as shown at block 96. In particular, the new desired temperature is programmed into the heater controller 16 as 37° C. Similarly, it is then verified that each of the slides reached 37° C.+/−2° C. as measured by the calibration sensor, as shown at block 98. A report is then printed listing the results of the calibration, as shown at block 100, and the calibration is done, as shown at block 102.

Figure 6A:
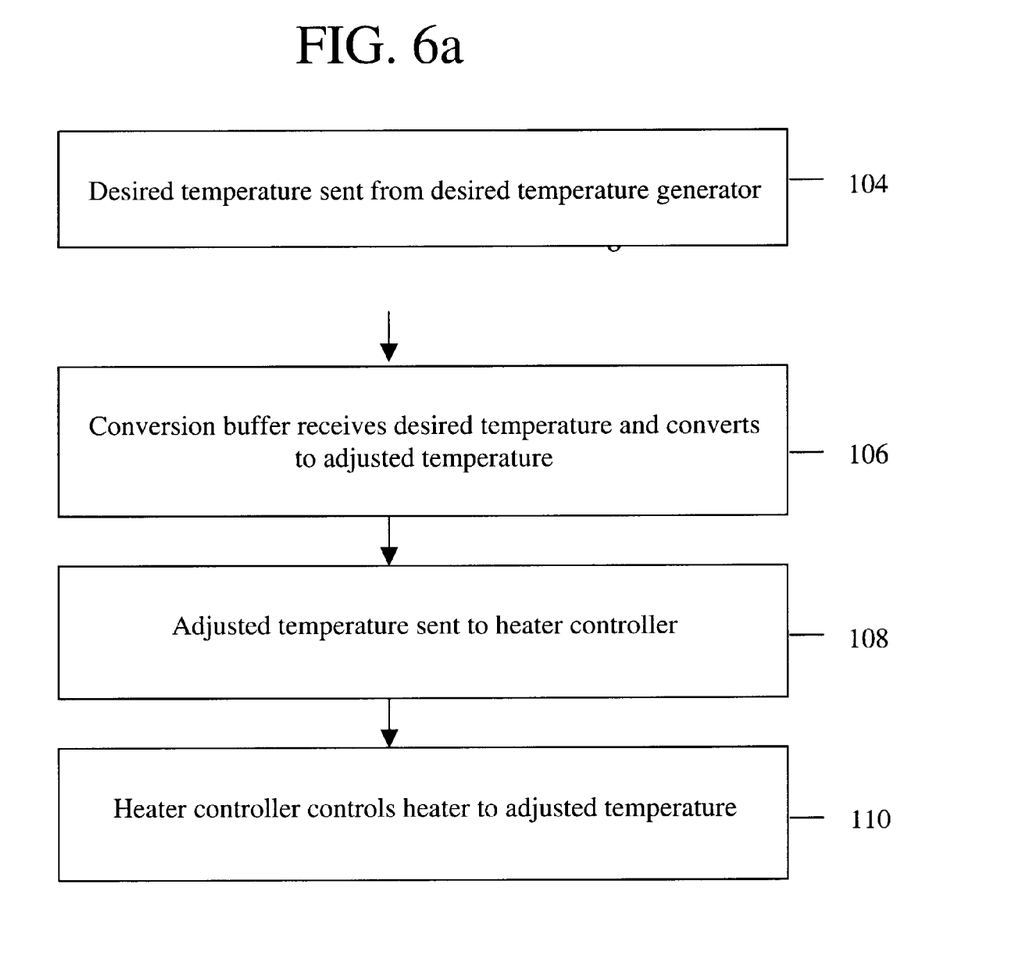
FIG. 6a is a flow chart of the modifying of the desired temperature to an adjusted temperature based upon the conversion buffer.

Once the conversion buffer 14 is generated, it is used to modify temperatures from the desired temperature generator 12 to the conversion buffer 14 and to modify readings from the heater controller 16 to the conversion buffer 14. Referring to FIG. 6a, there is shown a flow chart of the modifying of the desired temperature to an adjusted temperature, based upon the conversion buffer. The desired temperature generator 12 sends the desired temperature generator, as shown at block 104. The conversion buffer receives the desired temperature of the slide heater and converts the desired temperature to an adjusted temperature based upon the conversion buffer, as shown at block 106. The adjusted temperature is then sent to the heater controller, as shown at block 108. The heater controller then controls the heater to the adjusted temperature, as shown at block 110. In this manner, the temperature actually exposed to the slide, which is sitting on the heater, is to the desired temperature.

Figure 6B:
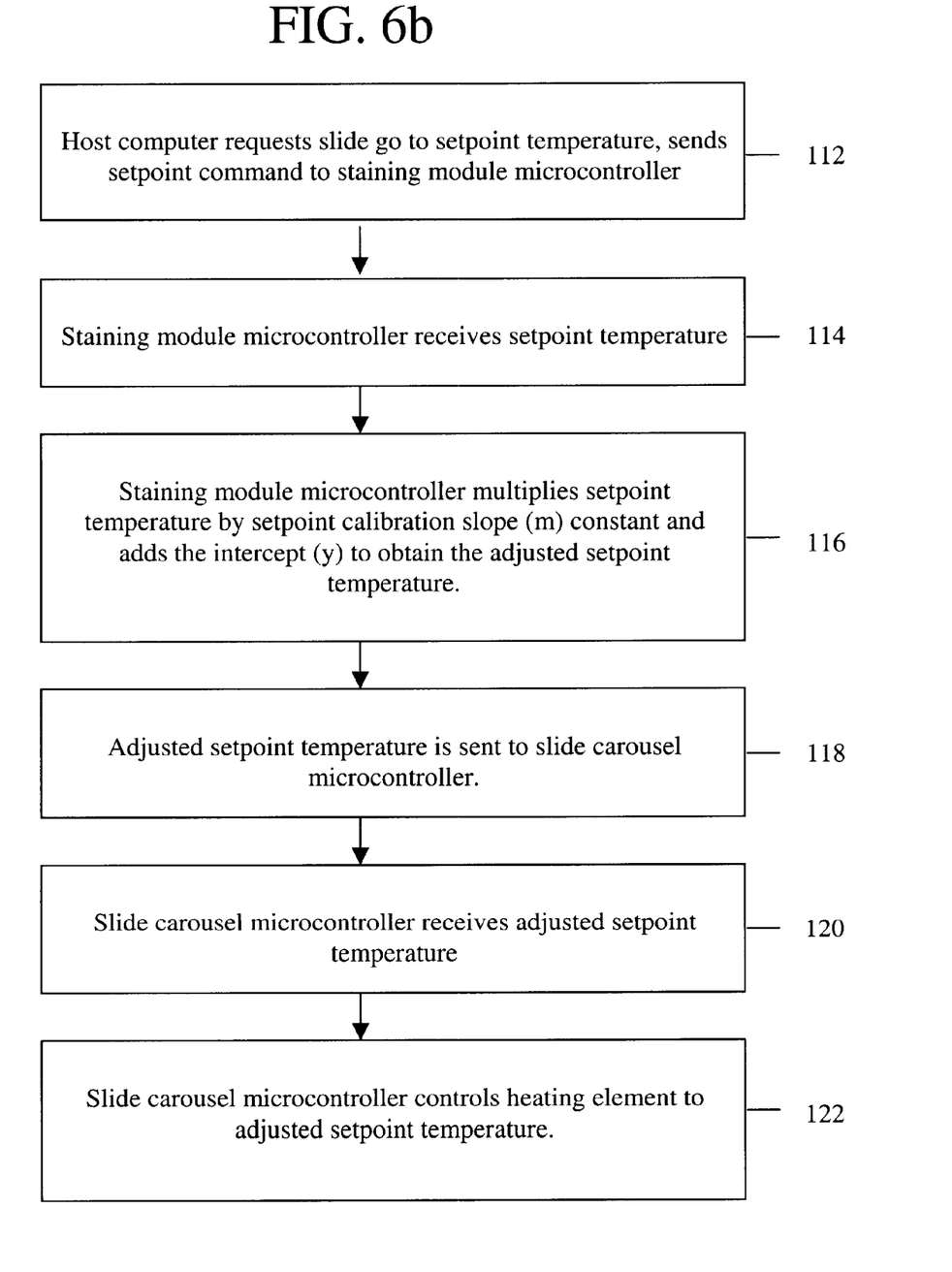
FIG. 6b is an expanded flow chart of the modifying of the desired temperature to an adjusted temperature, based upon the conversion buffer.

Referring to FIG. 6b, there is shown an expanded flow chart of the modifying of the desired temperature to an adjusted temperature, based upon the conversion buffer. The host computer requests the slide to go to the setpoint or desired temperature, sending the setpoint command to the staining module microcontroller, as shown at block 112. The staining module microcontroller receives the setpoint temperature, as shown at block 114. The staining module microcontroller reads the conversion buffer in its memory and multiplies the setpoint temperature by the setpoint calibratio slope (m) constant and adds the intercept (b) to obtain the adjusted setpoint temperature, as shown at block 116. The adjusted setpoint temperature is sent to the slide carousel microcontroller, as shown at block 118. The slide carousel microcontroller receives the adjusted setpoint temperature, as shown at block 120. And, the slide carousel microcontroller controls the heating element to the adjusted setpoint temperature, as shown at block 122.

Figure 7A:
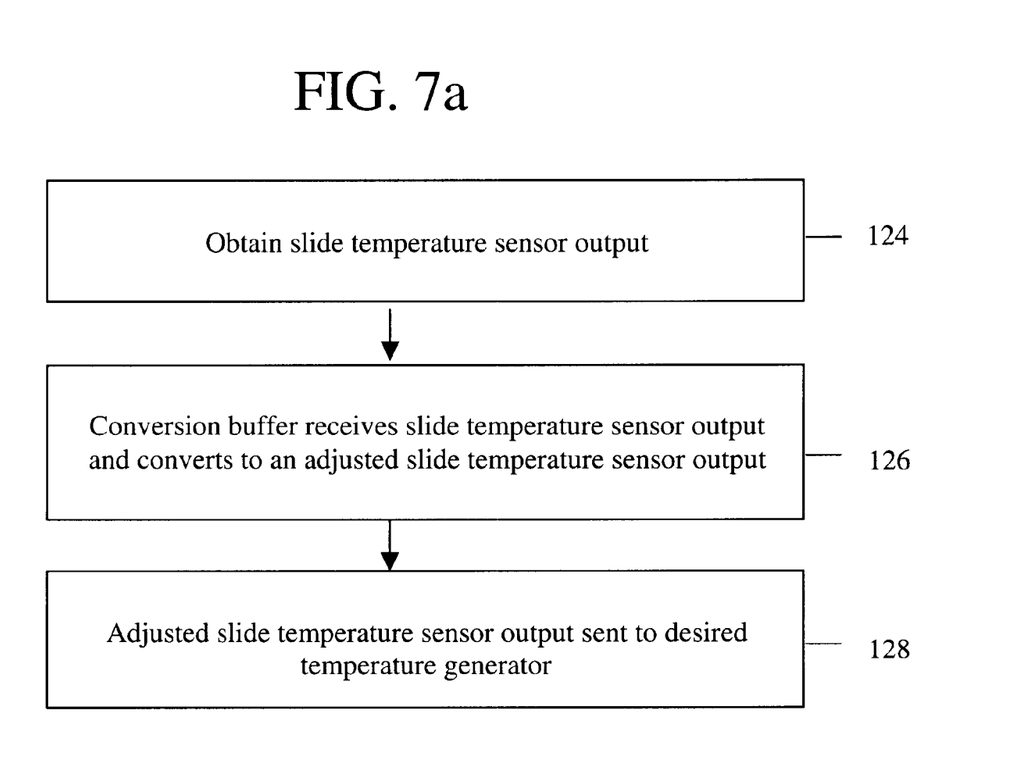
FIG. 7a is a flow chart of the modifying of the output of the slide temperature sensor to an adjusted sensor temperature output based upon the conversion buffer.

Referring to FIG. 7a, there is shown a flow chart of the modifying of the output of the slide temperature sensor to an adjusted sensor temperature output, based upon the conversion buffer. The output of the slide temperature sensor is obtained, as shown at block 124. The conversion buffer receives the slide temperature sensor output and converts it to an adjusted slide temperature sensor output, as shown at block 126. The adjusted slide temperature sensor output is then sent to the desired temperature generator, as shown at block 128.

Figure 7B:
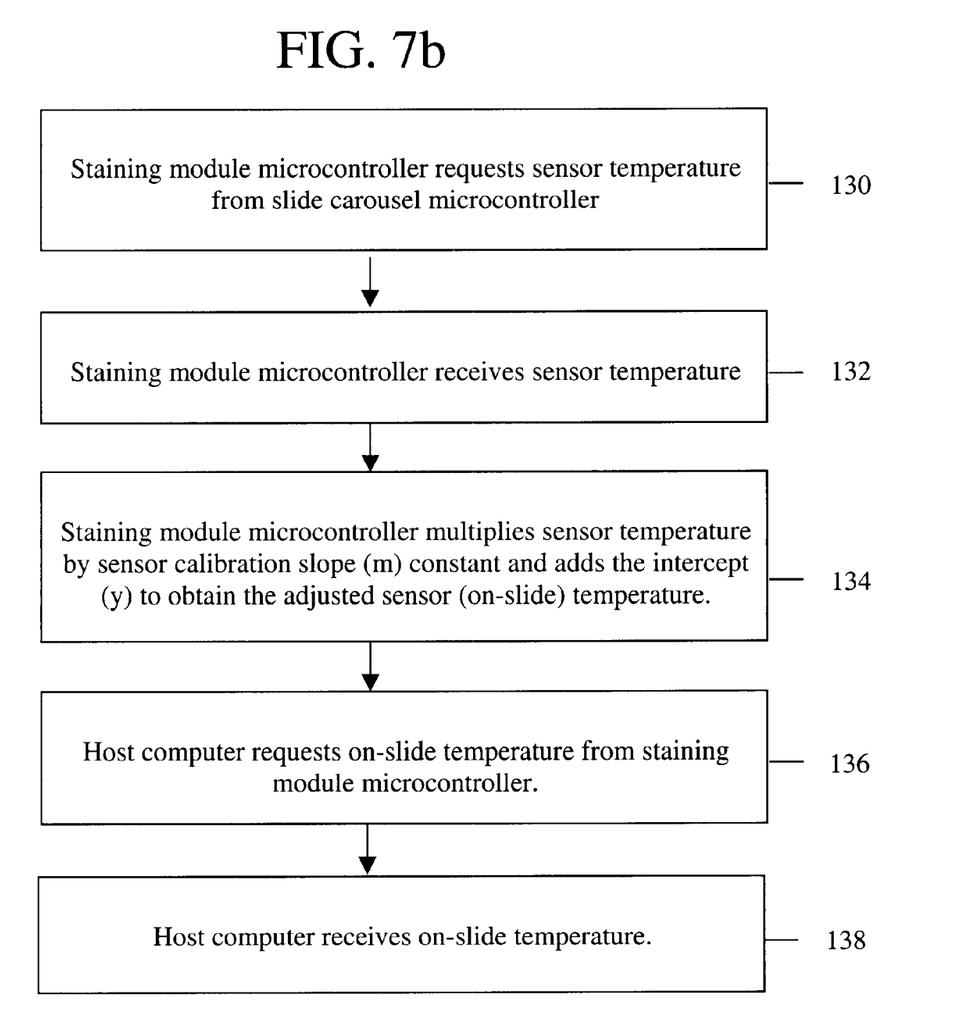
FIG. 7b is an expanded flow chart of the modifying of the output of the slide temperature sensor to an adjusted sensor temperature output based upon the conversion buffer.

Referring to FIG. 7b, there is shown an expanded flow chart of the modifying of the output of the slide temperature sensor to an adjusted sensor temperature output, based upon the conversion buffer. The staining module microcontroller requests sensor temperature from the slide carousel microcontroller, as shown at block 130. The staining module microcontroller receives the sensor temperature from the slide temperature sensor, as shown at block 132. The staining module microcontroller then multiplies the output of the sensor temperature by the sensor calibration slope (m) constant and adds the intercept (b) to obtain the adjusted (on-slide) temperature, as shown at block 134. The host computer requests the on-slide temperature from the staining module microcontroller, as shown at block 136. The host computer then receives the on-slide temperature, as shown at block 138.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A method for calibrating a slide heater for an automated biological apparatus, the slide heater having a slide calibration sensor and a slide temperature sensor, the method comprising the steps of:
   heating the slide heater to a first temperature;
   sensing at least one reading from the slide calibration sensor at a section of the slide heater where a slide sits;
   sensing at least one reading from the slide temperature sensor at a different section of the slide heater;
   heating the slide heater to a second temperature;
   sensing at least one reading from the slide calibration sensor at the section of the slide heater where the slide sits;
   sensing at least one reading from the slide temperature sensor at the different section of the slide heater;
   determining a conversion buffer based upon the readings from the slide calibration sensor and the slide temperature sensor.

2. The method of claim 1 wherein the conversion buffer is a straight line with two constants, a slope and a y-intercept.

3. The method of claim 1 wherein the section of the slide heater where the slide heater sits is on top of the slide heater.

4. The method of claim 3 wherein the different section of the slide heater is an underside of the slide heater.

5. A method for controlling a slide heater for an automated biological apparatus comprising the steps of:
   determining a conversion buffer based upon different temperature readings from a slide calibration sensor and a slide temperature sensor, the slide calibration sensor at a section of the slide heater where a slide sits, the slide temperature sensor at a different section of the slide heater;
   determining a desired temperature for the slide heater;
   converting the desired temperature to an adjusted temperature using the conversion buffer, the conversion buffer based upon calibration of the slide heater;
   receiving at least one reading from a slide temperature sensor for the slide heater; and
   controlling the slide heater based upon the at least one reading and based upon the adjusted temperature.

6. The method of claim 5 wherein the step of determining a desired temperature is performed by a host computer and further comprising:
   converting the at least one reading to an adjusted slide temperature sensor reading based upon the buffer conversion; and
   sending of the adjusted slide temperature sensor reading to the host computer.

7. The method of claim 5 wherein the conversion buffer is determined based upon the following calibration steps:
   heating the slide heater to a first temperature;
   sensing at least one reading from the slide calibration sensor at the section of the slide heater where a slide sits;
   sensing at least one reading from the slide temperature sensor at the different section of the slide heater;
   heating the slide heater to a second temperature;
   sensing at least one reading from the slide calibration sensor at the section of the slide heater where the slide sits; and
   sensing at least one reading from the slide temperature sensor at the different section of the slide heater.

8. A method for controlling a slide heater for an automated biological apparatus comprising the steps of:
   determining a conversion buffer based upon different temperature readings from a slide calibration sensor and a slide temperature sensor, the slide calibration sensor at a section of the slide heater where a slide sits, the slide temperature sensor at a different section of the slide heater;
   receiving at least one reading from a slide temperature sensor for the slide heater; and
   converting the at least one reading to an adjusted slide temperature sensor reading using the buffer conversion, the conversion buffer based upon calibration of the slide heater; and sending of the adjusted slide temperature sensor reading to a processor.

9. Apparatus for heating biological materials comprising a plurality of heaters;

a heater controller in communication with the plurality of heaters;

a plurality of slide temperature sensors in proximity to the plurality of heaters and in communication with the heater controller;

a conversion buffer in communication with the heater controller; and a desired temperature generator in communication with the conversion buffer;

wherein the conversion buffer is determined based upon different temperature readings from a slide calibration sensor and a slide temperature sensor, the slide calibration sensor at a section of the slide heater where a slide sits, the slide temperature sensor at a different section of the slide heater, and wherein the conversion buffer receives desired temperatures for each of the plurality of heaters from the desired temperature generator, converts the desired temperatures to adjusted temperatures based upon calibration of the heaters, and sends the adjusted temperatures to the heater controller for controlling the plurality of heaters at the adjusted temperatures.

10. The apparatus of claim 9 wherein the desired temperature generator is a host computer including a processor and a memory device.

11. The apparatus of claim 9 wherein the conversion buffer further receives readings from the plurality of slide temperature sensors, converts the readings to adjusted readings, and sends the readings to the desired temperature generator.

* * * * *